US009504537B2

(12) United States Patent
Johnson et al.

(10) Patent No.: US 9,504,537 B2
(45) Date of Patent: Nov. 29, 2016

(54) INTRA-ORAL DEVICE FOR PROTECTING ORAL TISSUES DURING RADIATION TREATMENT

(71) Applicant: GRAYDUCK STENTS, LLC, Seattle, WA (US)

(72) Inventors: Bart Johnson, Seattle, WA (US); Amy Winston, Seattle, WA (US)

(73) Assignee: GRAYDUCK STENTS, LLC, Seattle, WA (US)

( * ) Notice: Subject to any disclaimer, the term of this patent is extended or adjusted under 35 U.S.C. 154(b) by 0 days.

(21) Appl. No.: 13/684,528

(22) Filed: Nov. 24, 2012

(65) Prior Publication Data

US 2013/0131427 A1    May 23, 2013

Related U.S. Application Data

(63) Continuation-in-part of application No. 13/103,441, filed on May 9, 2011, now abandoned.

(60) Provisional application No. 61/347,985, filed on May 25, 2010.

(51) Int. Cl.
*A61F 5/56* (2006.01)
*A61C 5/14* (2006.01)
*A61N 5/10* (2006.01)

(52) U.S. Cl.
CPC . *A61C 5/14* (2013.01); *A61N 5/10* (2013.01); *A61N 5/1014* (2013.01); *A61B 2090/0436* (2016.02); *A61B 2090/0481* (2016.02); *A61N 2005/1094* (2013.01); *Y10T 29/52* (2015.01)

(58) Field of Classification Search
CPC .... A61F 5/56; A61F 5/566; A61M 16/0495; A61C 5/14; A61B 13/00

USPC .............. 128/859–862; 602/902; 433/6
See application file for complete search history.

(56) References Cited

U.S. PATENT DOCUMENTS 2,588,169 A * 3/1952 Shea .................. A61C 9/0006
433/140
4,156,424 A    5/1979 Burgin
(Continued)

OTHER PUBLICATIONS

Bankhead, Charles,Oral Shield Cuts Radiation to Normal Tissue; MedPage Today, Published: Jan. 31, 2012. http://www.medpagetoday.com/meetingcoverage/MHNCS/3093 (2 pages).
(Continued)

*Primary Examiner* — Victoria J Hicks
*Assistant Examiner* — Camtu Nguyen
(74) *Attorney, Agent, or Firm* — Schaffer IP Law, LLC

(57) ABSTRACT

An intra-oral device for positioning oral tissues during medical treatment, for example, radiation treatment. The device includes upper and lower dental arch members configured to engage the maxillary and mandibular teeth or edentulous arch(es) of a patient, respectively. The upper and lower dental arch members are operatively coupled to provide a dental arch assembly. A protective element to displace or depress a patient's tongue is secured at a suitable working position with respect to the dental arch assembly. In an embodiment, provision is made for three-dimensional spatial adjustment of the protective element to a desired location, at least during initial fitting and assembly. The device is then secured to allow consistent repetition of the oral tissue positioning from treatment to treatment. The protective element may be configured to engage the tongue of a patient so that the tongue may be selectively positioned for treatment and/or diagnostic procedures.

36 Claims, 10 Drawing Sheets

(56) References Cited

U.S. PATENT DOCUMENTS

| | | | |
|---|---|---|---|
| 4,337,765 A | | 7/1982 | Zimmerman |
| 4,676,240 A | | 6/1987 | Gardy |
| 5,190,990 A | | 3/1993 | Eichmiller |
| 5,550,383 A | * | 8/1996 | Haskell .................... C08K 3/08 250/515.1 |
| 5,678,993 A | * | 10/1997 | Jeffer ....................... A61C 8/00 433/168.1 |
| 5,988,170 A | * | 11/1999 | Thomas ......................... 128/848 |
| 6,976,491 B2 | | 12/2005 | D'Agosto |
| 7,520,281 B1 | | 4/2009 | Nahabedian |
| 7,607,439 B2 | | 10/2009 | Li |
| 2008/0308450 A1 | * | 12/2008 | Tchouangang ................ 206/570 |
| 2009/0241969 A1 | * | 10/2009 | Walker ................... A61F 5/566 128/848 |
| 2010/0294283 A1 | * | 11/2010 | Li ................................. 128/848 |
| 2011/0240036 A1 | | 10/2011 | Westbrook et al. |
| 2011/0291031 A1 | | 12/2011 | Johnson et al. |

OTHER PUBLICATIONS

Liao, J.; Johnson, B., Winston, A., et al, Customized Tongue-Displacing Dental Stents for Oral Mucosal Sparing and Immobilization in Head and Neck Radiotherapy, University of Washington, Seattle, Washington, http://astro2011.abstractsnet.com/pdfs/2592.pdf (1 page).

* cited by examiner

Copyright © 2012
by Grayduck Stents LLC

Copyright © 2012
by Grayduck Stents LLC

Copyright © 2012
by Grayduck Stents LLC

Copyright © 2012
by Grayduck Stents LLC

INTRA-ORAL DEVICE FOR PROTECTING ORAL TISSUES DURING RADIATION TREATMENT

RELATED PATENT APPLICATIONS

This application is a continuation-in-part and claims priority from currently pending U.S. patent application Ser. No. 13/103,441, filed May 9, 2011, which application claimed priority from U.S. Provisional Application No. 61/347,985, filed May 25, 2010. The disclosures of each of the aforementioned patent applications, including their specification, claims, and drawing figures, are hereby incorporated herein by this reference.

STATEMENT OF GOVERNMENT INTEREST

Not Applicable.

COPYRIGHT RIGHTS IN THE DRAWING

A portion of the disclosure of this patent document contains material that is subject to copyright protection. The patent owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This application relates to devices for reducing exposure of certain tissues to ionizing radiation during treatment of head and neck cancers in patients, and to methods for use of such devices.

BACKGROUND

As is generally known, cancer treatment can be complex and invasive. In some cases, patients need to be subjected to high-dose radiation treatment in order to eradicate and prevent additional cancerous tissue growth. In cases of head and neck cancer, cancerous tissue growth is typically located on the floor of the mouth, cheek lining, tonsils, pharynx, the tongue, and/or lymph nodes. When radiation treatment is applied in cases of head and neck cancer, some damage often occurs to non-cancerous tissues that lie in the pathway of the beam treating the cancer. For example, a patient's tongue may not be invaded by a cancer when the cancer is in the tonsils, but the tongue may be damaged by ionizing radiation that passes through the tongue in order to treat the tonsillar tumor. Thus, it would be advantageous if non-cancerous tissue could be spared radiation damage by altering the beam path, and/or by moving such non-cancerous tissue physically out of the way of the radiation beam.

BRIEF DESCRIPTION OF THE DRAWING FIGURES

Novel intra-oral devices will be described by way of exemplary embodiments, illustrated in the accompanying drawing figures in which like reference numerals denote like elements, and in which:

FIG. 1 shows, during fitting of a patient for use, a partial cross-sectional view of an embodiment for an intra-oral device for protecting oral tissues during radiation treatment, showing upper and lower dental arch members, a tongue-deviating paddle, and showing a midline rod in location for moving the tongue-deviating paddle for suitable tongue position adjustment, whether by in/out, up/down, or left/right movement of the tongue-deviating paddle, as further described herein.

FIG. 2 is a perspective view of an embodiment for an intra-oral device, showing upper and lower dental arch members, a left tongue-deviating paddle, and showing a midline rod in location for moving the left tongue-deviating paddle for suitable tongue position adjustment, whether by in/out, up/down, or left/right movement of the left tongue-deviating paddle, and the use of a posterior stabilizing rod, all as further described herein below.

FIG. 3 is a perspective view of an embodiment for an intra-oral device, showing upper and lower dental arch members, a tongue-depressing paddle, and showing a midline rod in location for moving the tongue-depressing paddle for suitable tongue position adjustment, whether by in/out, up/down, clockwise/counterclockwise rolling movement, or left/right movement of the tongue-depressing paddle, and the use of first and second posterior stabilizing rods, each of which may, in an embodiment, be moved in/out, up/down, or left/right, or rolled for suitable positioning of the tongue-depressing paddle.

FIG. 4 is an exploded perspective view of an embodiment for an intra-oral device, showing upper and lower dental arch members which are joined to form a dental arch assembly, a tongue-depressing paddle, and showing a midline rod in location for assembly through an adjustable guide portion (that is, disposed so as to tie parts together in a manner that allows motion between the dental arch assembly and the tongue-depressing paddle) and attachment of the midline rod to the tongue-depressing paddle for suitable tongue position adjustment, whether by in/out, up/down, or left/right movement of the tongue-depressing paddle, and the provision of first and second posterior stabilizing rods in location for assembly in each case through an adjustable guide portion and attachment to a left side and a right side of the tongue-depressing paddle, respectively.

FIG. 5 is a partially assembled exploded perspective view of an embodiment for an intra-oral device, similar to that just shown in FIG. 4, showing upper and lower dental arch members which are joined to form a dental arch assembly, and now showing a tongue-depressing paddle in an initial position with first and second posterior stabilizing rods in location assembled through an adjustable guide portion and attached to a left side and a right side of the tongue-depressing paddle, respectively, and also showing a midline rod attachment of the midline rod yet to be inserted through an adjustable guide portion and affixed to a tongue-depressing paddle for suitable tongue position adjustment in a patient.

FIG. 6 is a perspective view taken looking down and from the rear at an embodiment of a fully assembled intra-oral device, similar to that just shown in FIGS. 4 and 5, showing upper and lower dental arch members which are joined to form a dental arch assembly, and now showing a tongue-depressing paddle in an initial position with first and second posterior stabilizing rods in location assembled each through an adjustable guide portion and attached to a left side and to a right side of a tongue-depressing paddle, respectively, and also showing a midline rod attachment of the midline rod inserted through an adjustable guide portion and affixed to a tongue-depressing paddle for suitable tongue position adjustment in a patient.

FIG. 7 is a side view taken looking from the rear at an embodiment of a fully assembled intra-oral device, similar to that just shown in FIGS. 4, 5, and 6, here showing upper and lower dental arch members which are joined to form a dental arch assembly, and now showing a tongue-depressing paddle in an initial position with first and second posterior stabilizing rods in location assembled each through an adjustable guide portion and attached to a left side and to a right side of a tongue-depressing paddle, respectively, and also showing a midline rod attachment of the midline rod inserted through an adjustable guide portion and affixed to a tongue-depressing paddle for suitable tongue position adjustment in a patient, which in this view with the posterior stabilizing rods in a dihedral configuration wherein they slope downwardly from their respective adjustable guide portions at the dental arch assembly to their respective attachment points to the tongue-depressing paddle.

FIG. 8 is a partially exploded perspective view of an embodiment for an intra-oral device, showing major components for attachment of a left tongue-displacing paddle to a dental arch assembly, illustrating the use of first or right side posterior stabilizing rod in location assembled through an adjustable guide portion and attached to the right side of the left tongue-displacing paddle, and also showing a midline rod attached to a front rod receiving receptacle in the left tongue-displacing paddle, and configured for insertion of the midline rod through an adjustable guide portion in the dental arch assembly.

FIG. 9 is a perspective view of an embodiment for an intra-oral device, showing major components used in the attachment of a left tongue-displacing paddle to a dental arch assembly, illustrating the use of first or right side posterior stabilizing rod in location assembled through an adjustable guide portion and attached to the right side of the left tongue-displacing paddle, and also showing a midline rod attached to a front rod receiving receptacle in the left tongue-displacing paddle, and wherein the midline rod has been inserted through an adjustable guide portion in the dental arch assembly, and also noting a location in broken lines where the midline rod and posterior stabilizing rod may be shortened as desirable for convenient repeated use and/or for storage of the intra-oral device.

FIG. 10 is a perspective view of an embodiment for an intra-oral device similar to that just shown in FIG. 9, looking down at the intra-oral device, now showing major components used in the attachment of a left tongue-displacing paddle to a dental arch assembly, illustrating the use of first or right side posterior stabilizing rod in location assembled through an adjustable guide portion and attached to the right side of the left tongue-displacing paddle, and also showing a midline rod attached to a front rod receiving receptacle in the left tongue-displacing paddle, and wherein the midline rod has been inserted through an adjustable guide portion in the dental arch assembly, and also illustrating that for a given patient, the midline rod and posterior stabilizing rod each can be shortened for convenient repeated use and/or for storage of the intra-oral device.

FIG. 11 is a perspective view of an embodiment for an adjustable guide portion that may be used in an embodiment for an intra-oral device, a ball-type joint with range of motion to a limit of the freedom of movement of the joint (here the outer broken line circle), as, for example, may be provided in a spherical bearing within a housing and, in an embodiment further including a sleeve with fastener for securing a rod passing through it which provides freedom to alter the selected location for a rod as regards translation along the rod's longitudinal axis (i.e. in-out movement along the rod), and further illustrating a rod located in the adjustable guide (either during an adjustment or fitting phase, or after being secured, longitudinally) may be adjusted in a pitch axis motion (tongue deviating paddle moves up/down), or along a yaw axis motion (tongue deviating paddle moves left/right), or along a roll axis motion (top and bottom of the rod, and of the tongue deviating paddle, move in opposite directions as they are rolled).

FIG. 12 provides a conceptual illustration of an optional coupling joint for joining an upper dental arch member (upper horseshoe) with a lower dental arch member to form a dental arch assembly.

Figure 14:
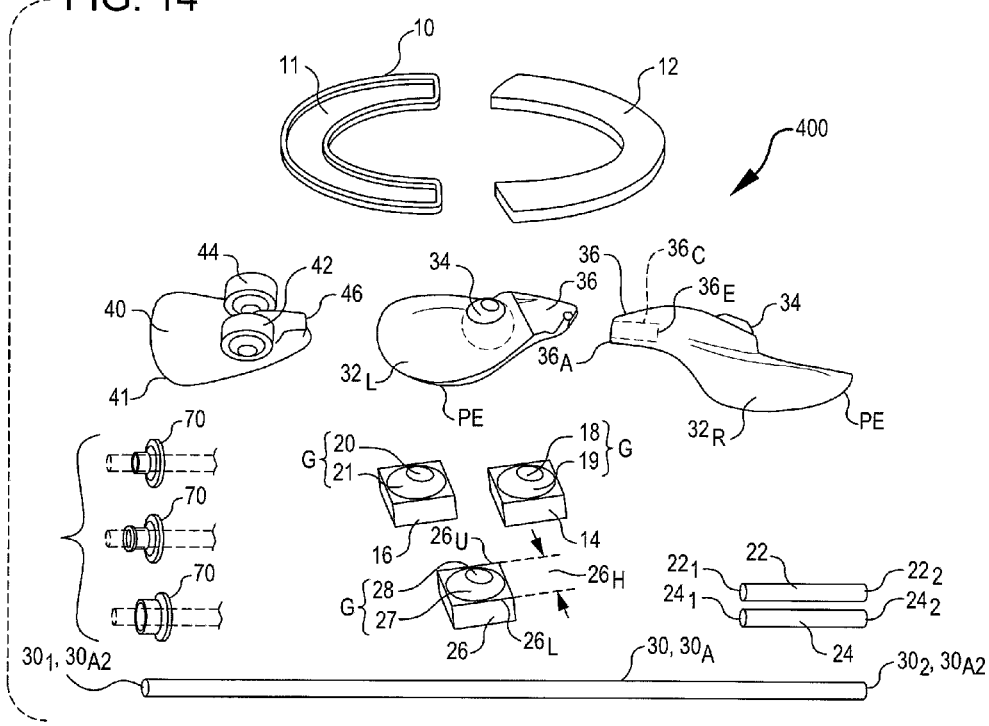

FIG. 14 illustrates an embodiment for a kit including various components that may be selected for assembly into an intra-oral device for protecting oral tissues during radiation treatment generally according to configuration(s) described herein; the kit includes upper and lower dental arch members, a tongue-depressing paddle, a left tongue-deviating paddle, a right tongue-deviating paddle, a pair of posterior struts, an anterior strut, posterior stabilizing rods, a midline rod, and optionally a plurality of locking mechanisms.

Figure 15A:
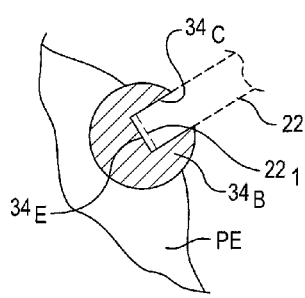

FIG. 15A is a cross section of a mount for use on a tongue-deviating paddle, including a spherical or ball joint that has a seat for a posterior stabilizing rod.

Figure 15B:
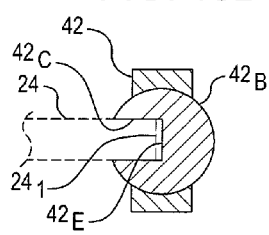

FIG. 15B is a cross section of a mount for use on a first side of a tongue-depressing paddle, including spherical or ball joint that has a seat for a posterior stabilizing rod.

Figure 15C:
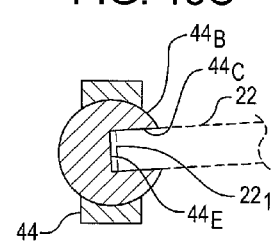

FIG. 15C is a cross section of a mount for use on a second side of a tongue-depressing paddle, including spherical or ball joint that has a seat for a posterior stabilizing rod.

The foregoing figures, being merely exemplary, contain various elements that may be present or omitted from actual apparatus that may be constructed, or used to practice the methods taught herein, and to manufacture the intra-oral devices as set forth herein. An attempt has been made to draw the figures in a way that illustrates at least those elements that are significant for an understanding of the devices taught herein, and for the alternate configurations thereof, and for the methods of use of the devices. However, various other elements for such intra-oral devices, for the methods of use thereof, may be utilized, within the teachings hereof and within the coverage of the claims set forth herein.

DETAILED DESCRIPTION

Figure 1:
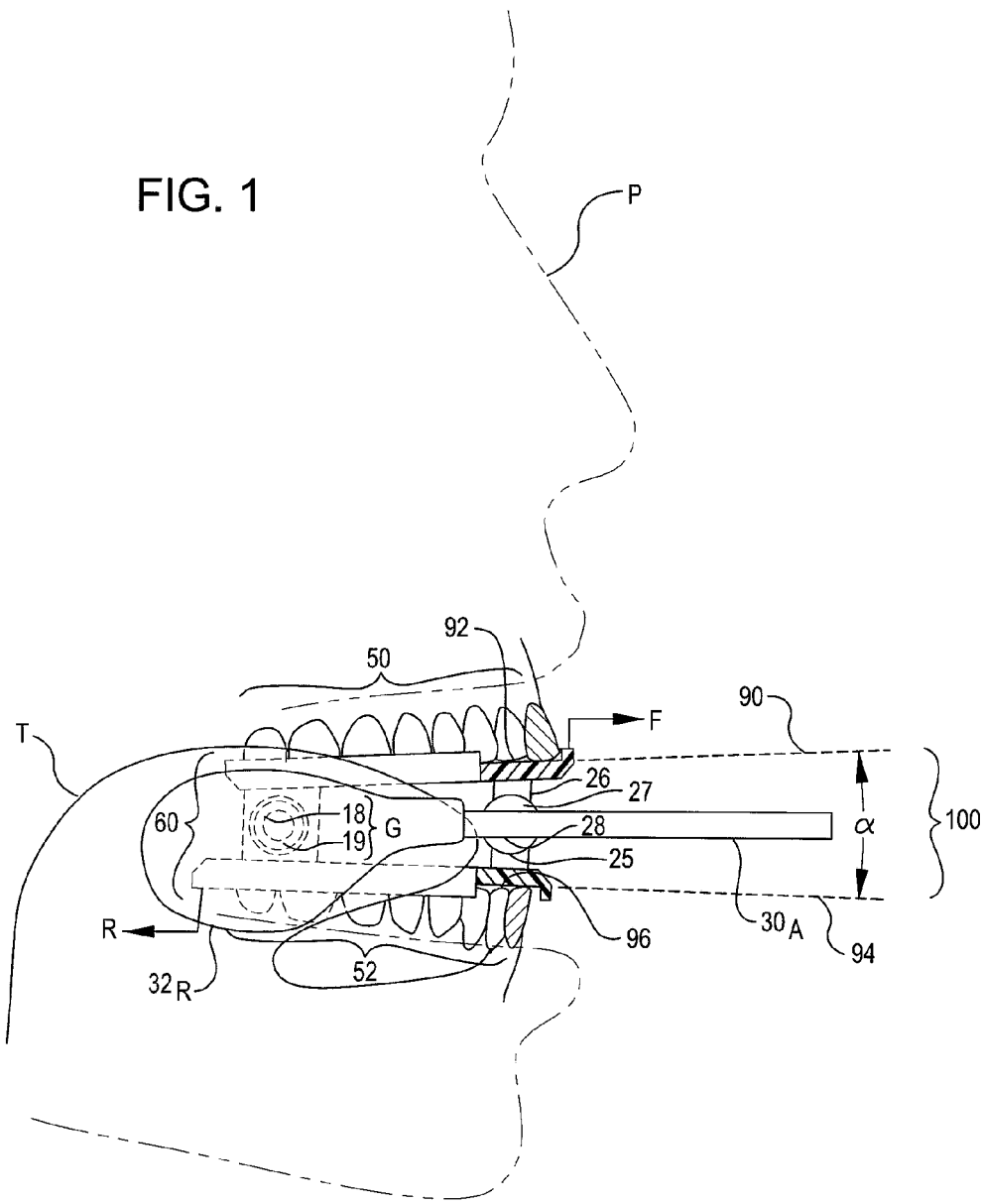
Figure 2:
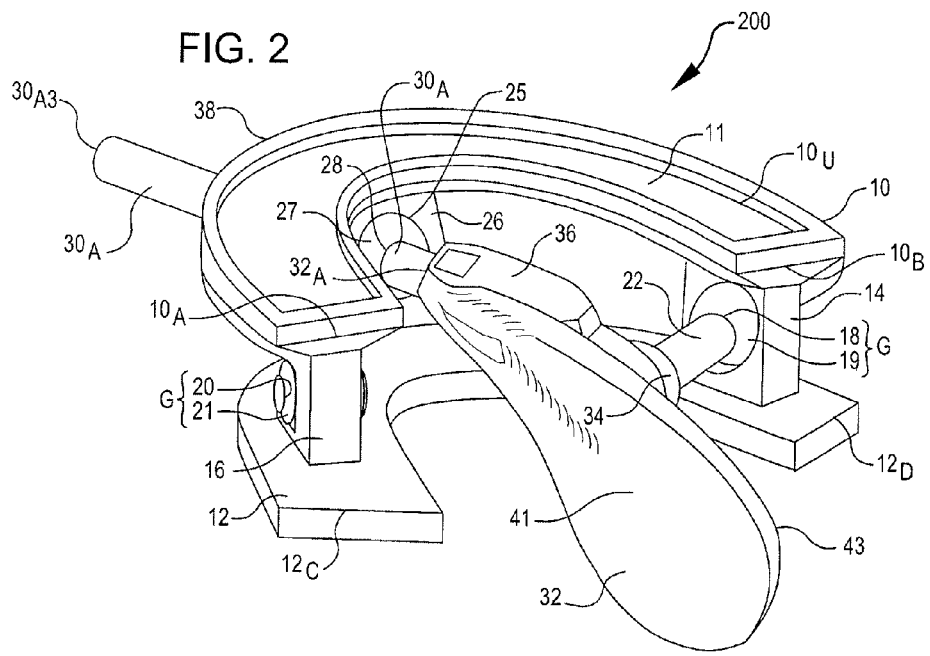
Figure 3:
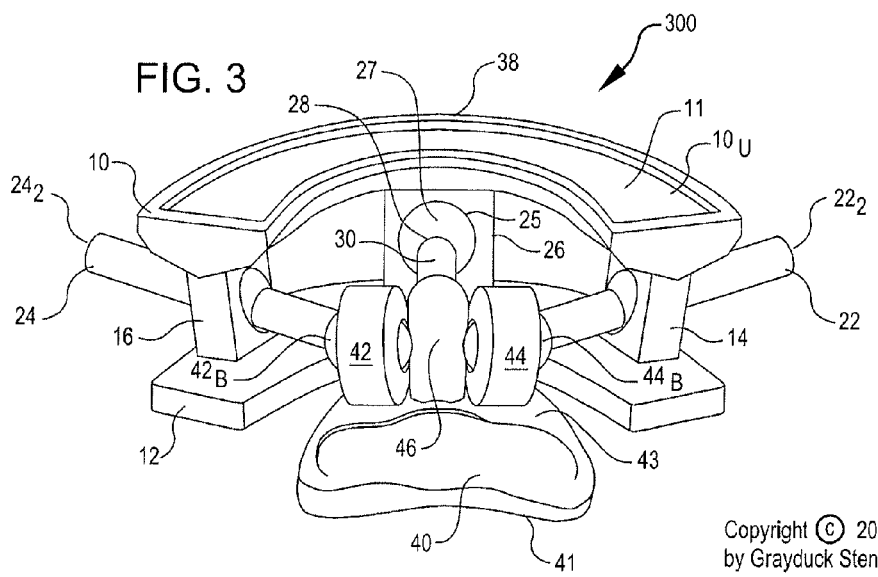

Intra-oral devices for protecting head and neck tissues during radiation treatment, and method(s) for use of various embodiments for such devices, are described herein. In FIG. 1, an intra-oral device 100 is shown being fitted to a patient P for movement of the patient's tongue T, which may be envisaged from the illustration to be, in an embodiment, to the patient's right. In FIG. 2, a substantially mirror image configuration to intra-oral device 100 just noted above is provided in the form of an intra-oral device 200; the intra-oral device 200 is configured for movement of a patient P's tongue T to the left. In FIG. 3, an intra-oral device 300 is depicted which is configured for guiding movement of a patient P's tongue T downward. Such intra-oral devices 100, or 200, or 300, or similar embodiments using the teachings hereof, may be useful in the reduction of damage to non-cancerous tissues of an oral cancer patient during radiation treatment. The intra-oral devices 100 or 200 provide structures such as tongue deviation paddle $32_R$ (for movement of a patient's tongue to the right), or tongue deviation paddle $32_L$ (for movement of a patient's tongue to the left) either of which can move a patient's tongue out of the way of a radiation beam during treatment. The intra-oral device 300 may include a tongue-depressing paddle 40 which may be used to depress a patient P's tongue T out of the way of a radiation beam during treatment. Structures such as tongue-deviation paddles $32_L$ or $32_R$ (which generally may be referenced herein without regard to "handedness" as tongue-deviation paddle 32) or a tongue-depressing paddle 40, may also hold a patient's tongue T or other adjacent tissues steady in a repeatable position so that a multi-dose radiation beam can be better targeted. Use of such intra-oral devices minimizes exposure and resulting damage from radiation to adjacent non-cancerous tissues. In various embodiments, and in methods of use thereof, intra-oral devices 100, or 200, or 300, or other embodiments and configurations described herein, may be configured to protect a patient's healthy tongue from the negative effects of radiation. In other embodiments, and methods of use thereof, intra-oral devices 100, or 200, or 300, or other embodiments and configurations made possible by the descriptions herein, may be configured to stabilize a cancerous lesion on a patient's tongue so that a radiation beam will have a relatively fixed, stable target volume during radiation treatment.

As just mentioned above, one component useful in an embodiment of intra-oral devices 100 or 200 which provides tongue-deviating functionality is a tongue-deviating paddle $32_R$ or $32_L$. Such a tongue-deviating paddle $32_R$ or $32_L$ may be disposed in a roughly vertical configuration, such as depicted in FIGS. 1 and 2. However, note that the tongue-deviating paddles need not be oriented roughly vertically, and may be rotated to any desired angle. As noted in FIG. 1, and elsewhere herein, a tongue-deviating paddle noted with reference numeral $32_R$ may be configured for urging a tongue to a patient's right. For example, as noted in FIG. 2 and elsewhere herein, a tongue-deviating paddle noted with reference numeral $32_L$ may be configured for urging a tongue to a patient's left. In an embodiment, one of the uses of a tongue-deviating paddle, whether $32_R$ or $32_L$, is to move a patient's tongue away from a side of the patient's mouth that has a cancer to be treated by radiation. Various embodiments for an intra-oral device 100 or 200 may be configured such that the position of a tongue-deviating paddle $32_R$ or $32_L$ may be adjusted to allow for customizing the device 100 or 200 to the particular size and shape of the mouth and tongue of a particular patient.

Additionally, in an embodiment of an intra-oral device 100 or 200, a tongue-deviating paddle $32_R$ or $32_L$ may be alternately be disposed substantially horizontally in order to depress, raise, or otherwise stabilize the patient's tongue. In such manner, the positioning of tongue-deviating paddle $32_R$ or $32_L$ may optionally also include support of a tongue toward one side or another of a patient's mouth. Thus, in an embodiment for an intra-oral device 100 or 200, a tongue-deviating paddle $32_R$ or $32_L$ may be disposed substantially horizontally, to upwardly lift a tongue, or to downwardly depress a tongue, in order to hold a patient's tongue away from a cancerous zone in the patient's mouth, so as to minimize or prevent exposure of a patient's tongue or other tissues to radiation.

Intra-oral devices 100, 200, 300, or alternate embodiments according to the teachings hereof, may be provided in, or assembled from kits 400 as noted in FIG. 14, having components of various predetermined sizes. For example, small sized components, with small upper 10 and lower 12 dental arch members in a dental arch assembly 60, with small tongue-deviating paddles $32_L$ and $32_R$ and a small tongue-depressing paddle 40 may be provided. In another embodiment, medium sized components may be provided, with medium sized upper 10 and lower 12 dental arch members in a dental arch assembly 60, and medium sized tongue-deviating and/or medium size tongue-depressing paddles. In other embodiments, large sized components may be provided, having large upper 10 and lower 12 dental arch members in a dental arch assembly 60, and large tongue-deviating 32 and/or tongue-depressing paddles 40, all of which may be adapted for different sizes and shapes of mouths encountered in various patients P to be treated. Yet further, embodiments may be configured in a mix-match combination, mixing large, medium, or small components, to accommodate unusual mouth sizes or treatment environments as may be encountered in various patients. As depicted in FIG. 14, a kit 400 for fabrication of an intra-oral device 100, or 200, or 300 may include various components, and selected components may be assembled into an embodiment having primarily tongue-deviating functionality, or into an embodiment having primarily tongue-depressing functionality.

Attention is directed to FIG. 3, which shows an intra-oral device 300 having a tongue-depressing function, using a tongue-depressing paddle 40. The purpose of the tongue-depressing paddle 40 is to move a patient's tongue down, for example during treatment of a maxillary cancer, or to stabilize a patient's tongue in a secure position, for example during treatment of a mandibular or tongue cancer. The intra-oral device 300 may be configured such that the position of a tongue-depressing paddle 40 may be adjusted to allow for customizing to the particular size and shape of the mouth, and size and shape of a tongue, of a particular patient.

In various embodiments, an upper dental arch member 10 may be separately provided. In a kit 400 (e.g., see FIG. 14), a selection of upper dental arch members 10 may be provided in preselected sizes, having a configuration complementary in size and shape to that of maxillary dental arch dimensions found in a selected group of anticipated patients. In an embodiment, an upper dental arch member 10 may be provided in a generally U-shaped (e.g., horseshoe shaped) configuration. An upper dental arch member 10 may be provided in various sizes, such as small, medium, large, or other sizes.

Figure 13A:
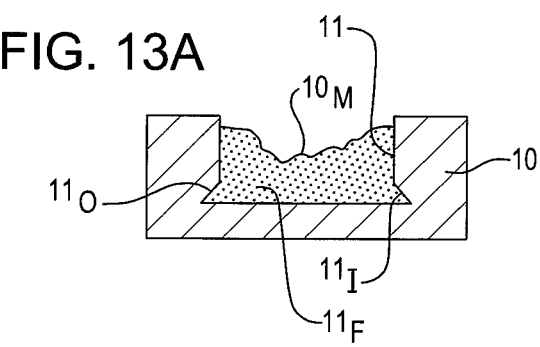
FIG. 13A is a cross section of an upper dental arch member, taken as at line 13A-13A of FIG. 4, which configuration may be provided in an embodiment for an intra-oral device, showing an upper receiving trough (which may include slots or holes) in the upper dental arch member which may be filled with a fill-in material molded to fit a particular patient's teeth or edentulous arch(es).

As may be appreciated from FIGS. 2, 3, 4 and 13A, in an embodiment, an upper dental arch member 10 may have an upper side $10_U$. An upwardly directed upper receiving trough 11 may be disposed on or in the upper side $10_U$. As seen in FIG. 13A, the upper receiving trough 11 may be adapted to receive a fill-in material $11_F$, which fill-in material $11_F$ may be molded to customize the fit of the upper dental arch member 10 to an individual patient's maxillary teeth 50 (see FIG. 1) or edentulous maxillary arch. The upper receiving trough may be variously adapted to receive a moldable compound for fabrication into a bite pad for secure receipt of the occlusal surface of a patient's maxillary teeth or edentulous arch. Optionally, as seen in FIG. 13A, in order to assist in the retention of the fill-in material $11_F$ in the upper receiving trough 11, an inwardly directed wedge $11_I$ and/or an outwardly shaped wedge $11_O$ may be provided, such as by way of post molding machining of upper dental arch 10, or by using multipart fabrication techniques.

In various embodiments, a lower dental arch member 12 may be provided. In a kit 400 (see FIG. 14), a selection of various sizes for a lower dental arch member 12 may be provided in a configuration complementary in size and shape to that of mandibular dental arch dimensions expected to be found in an anticipated patient population. In an embodiment, a lower dental arch member 12 may be provided in a generally U-shaped (e.g., horseshoe shaped) configuration. A lower dental arch member 12 may be provided in various sizes, such as small, medium, large, or other sizes.

Figure 7:
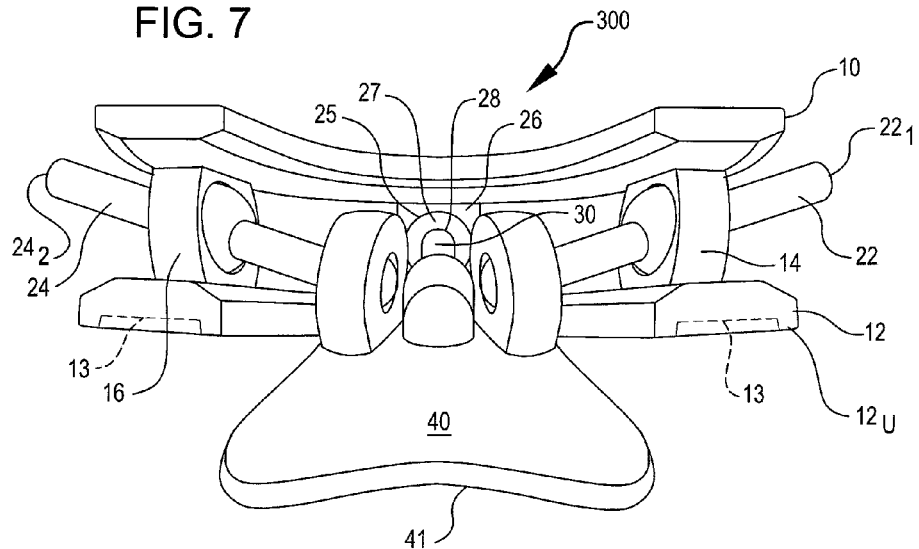
Figure 8:
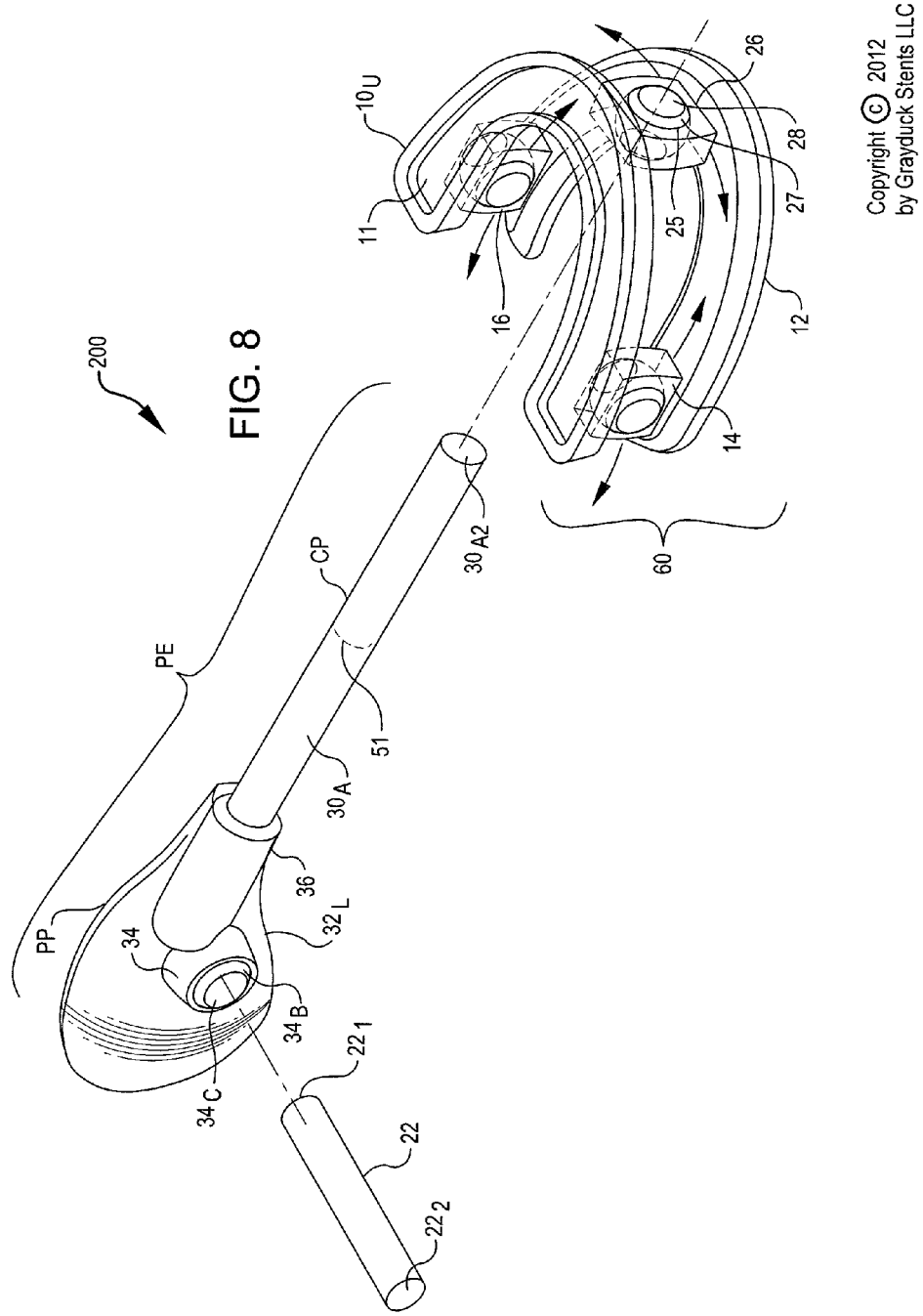
Figure 9:
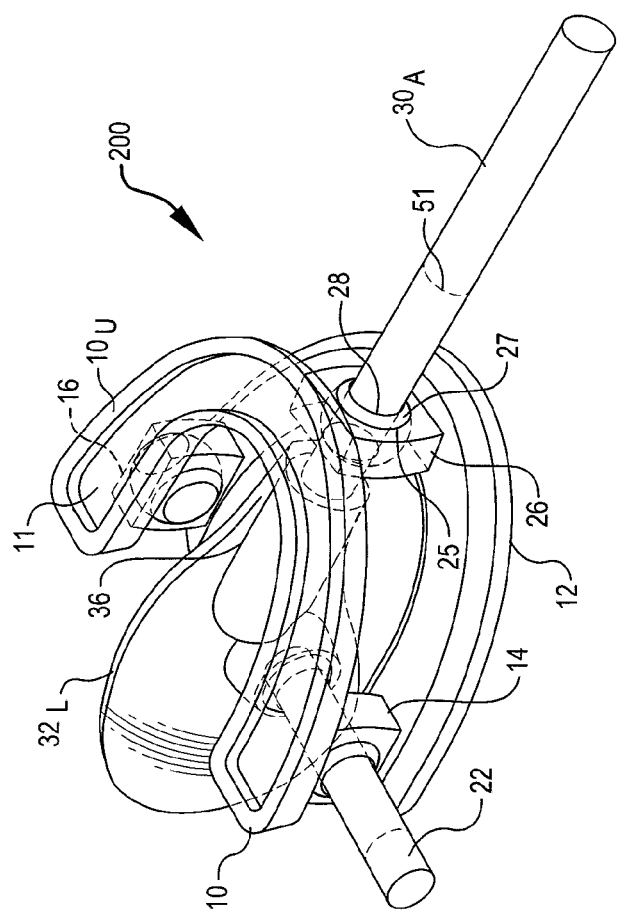
Figure 10:
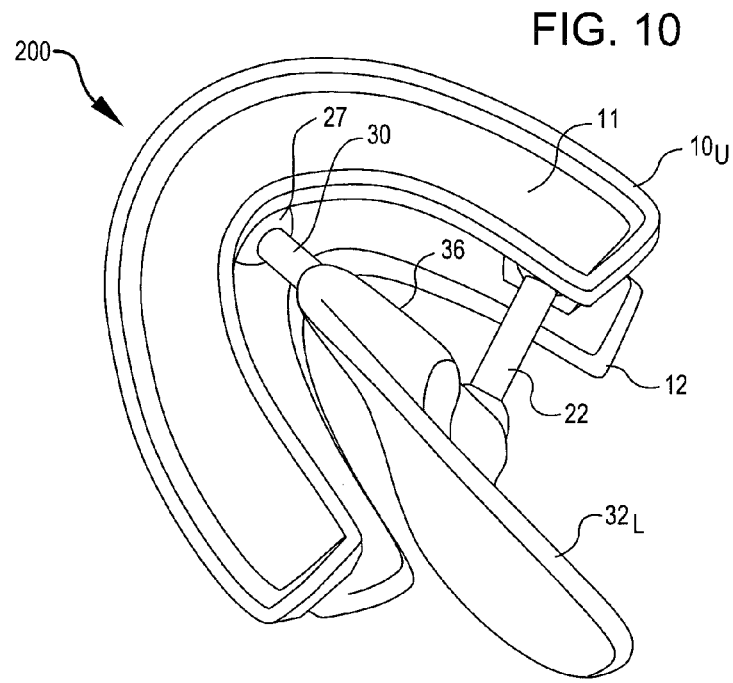
Figure 13B:
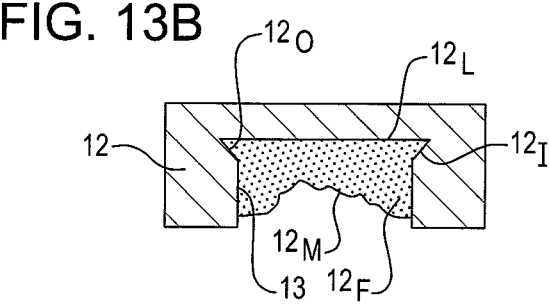
FIG. 13B is a cross section of a lower dental arch member, taken as at line 13B-13B of FIG. 4, which configuration may be provided in an embodiment for an intra-oral device, showing a lower receiving trough (which may include slots or holes) in the lower dental arch member which may be filled with a fill-in material molded to fit a particular patient's teeth or edentulous arch(es).

As may be appreciated from FIGS. 1, 7, and 13B, in an embodiment, a lower dental arch member 12 may have a lower side $12_L$ on or in which a downwardly directed lower receiving trough 13 is provided. The downwardly directed receiving trough 13 may be adapted to receive a fill-in material $12_F$, which fill-in material $12_F$ may be molded to customize the fit of the lower dental arch member 12 to an individual patient's mandibular teeth 52 (see FIG. 1) or edentulous mandibular arch. The lower receiving trough 13 may be variously adapted to receive a moldable compound for fabrication into a bite pad for secure receipt of the occlusal surface of a patient's mandibular teeth or edentulous arch. Optionally, as seen in FIG. 13B, in order to assist in the retention of the fill-in material $12_F$ in the lower receiving trough 13, an inwardly directed wedge $12_I$ and/or an outwardly shaped wedge $12_O$ may be provided, such as by way of post molding machining of lower dental arch 12, or by using multipart fabrication techniques.

In various embodiments, the upper dental arch member 10 and the lower dental arch member 12 are joined together to provide a dental arch assembly 60. As seen in FIG. 2, in an embodiment, the upper dental arch member 10 may be connected to the lower dental arch member 12 by an anterior strut 26. In an embodiment, posterior struts 14 and 16 may connect the upper dental arch member 10 and lower dental arch member 12. As noted in FIG. 2, in an embodiment, upper dental arch member 10 may include a first end $10_A$ and a second end $10_B$. In an embodiment, the lower dental arch member 12 may include a third end $12_C$ and a fourth end $12_D$. The upper dental arch member 10 and the lower dental arch member 12 may be joined to each other at, near, or adjacent their respective posterior aspect (that is, the open end of their "U" shape). On one side, at, adjacent, or near first end $10_A$ and third end $12_C$, upper member 10 and lower member 12 may be joined together. On an opposing side, at, adjacent, or near second end $10_B$ and fourth end $12_D$, upper member 10 and lower member 12 may be joined together.

In an embodiment, as seen in FIGS. 2-9, struts 14 and 16 may allow anterior-posterior placement at selected locations between the upper dental arch member 10 and the lower dental arch member 12. Thus, the upper dental arch member 10 and the lower dental arch member 12 may be moved forward F or rearward R with respect to each other as noted by reference arrows in FIG. 1. In an embodiment, provision of adjustable struts 14 and 16 (for example, sliding or hinged components for attachment to one or both of the upper dental arch member 10 and lower dental arch member 12) may allow adjustment for a fabricating a dental arch assembly with regard to the amount of interincisal opening.

As seen in FIGS. 2 and 3, an embodiment, the struts 14 and 16 may include therein an adjustable guide G, which may be provided in the form of a spherical bearing or ball joint 19 and 21, respectively. Such ball joints 19 and 21 may have therein a through joint aperture such as a slot or hole defined by internal sidewall 18 or 20, respectively, which allow a tongue-deviating paddle 32 or tongue-depressing paddle 40 to be adjusted in a medial and/or lateral direction (that is, in a front to back or in a side to side fashion), an in various embodiments, in up and down directions as well.

In an embodiment, at time of fabrication the struts 14 and 16 may be adjustable so as to allow the fabricator to conform the upper dental arch member 10 and lower dental arch member 12 to a patient's jaw and/or tongue shapes, or treatment objectives. In such embodiment, at time of fabrication, the struts 14 and/or 16 may be moved forward or backward, so as to configure the upper dental arch member at a suitable location relative to the lower dental arch member.

Attention is now directed to FIG. 3, where posterior stabilizing rods 22 and 24 are shown. Rods 22 and 24 provide structural connector, for example between dental arch 60 and tongue-deviating paddle 32 or tongue-depressing paddle 40. Rods 22 and 24 may be sized and shaped to be inserted through the through joint aperture such as slots or holes defined by sidewalls 18 and/or 20 in the ball joints 19 and/or 21 of struts 14 and/or 16. As seen in FIG. 3, posterior stabilizing rods 22 and 24 may be utilized to locate and secure a tongue-depressing paddle 40. Alternately, as depicted in FIG. 2, a posterior stabilizing rod such as rod 22 may be utilized to locate and secure a tongue-deviating paddle 32.

Figure 11:
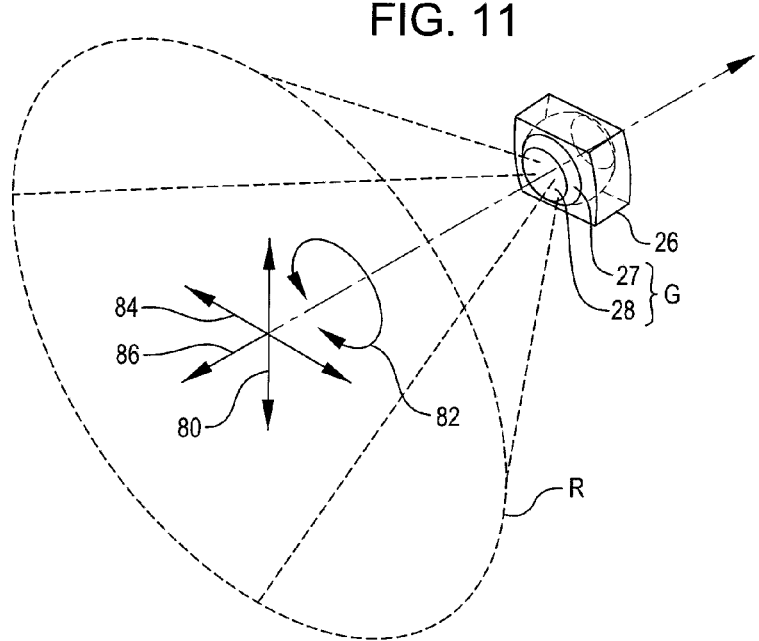

As seen in FIG. 2, at the anterior aspect, that is, at the front 38 of the device, an anterior strut 26 may be attached to join the upper member 10 and the lower member 12 in such a way that the anterior strut 26 may be provided of selected height $26_H$ between a lower side $26_L$ placed at lower dental arch member 12, and an upper side $26_U$ placed at upper dental arch member 10 (see FIG. 14), and thus can adjustment may be tolerated with respect to differences in the interincisal distance in various patients. An anterior strut 26 may also provide a housing 25 for a rotating spherical bearing or ball joint 27 that may have a running through it a guide hole or slot defined by interior sidewalls 28. The anterior strut 26 may be configured to support and serve as an attachment point as regards the anterior/posterior location of a tongue-deviating paddle 32 or a tongue-depressing paddle 40. The anterior strut 26 may also be configured to support and serve as an X, Y and Z axis placement locator for a tongue-deviating paddle 32 or a tongue-depressing paddle 40. For example, see FIG. 11, wherein a range of motion limit R for an exemplary adjustable guide G such as ball joint 27 in strut 26 is illustrated (functionality may be similar for adjustable guides G in struts 14 and 16). In an embodiment, a connector portion CP is sized and shaped for adjustable engagement with the adjustable guide G. In an embodiment, such adjustable guides G may allow adjustment along one or more of (a) a pitch axis 80, (b) roll axis 82, (c) yaw axis 84, and (d) a linear axis 86. As shown in FIG. 2, a midline rod 30 may provided sized and shaped complementary to a through joint aperture slot or hole defined by sidewalls 28 in ball joint 27 of anterior strut 26, to connect, locate, and secure a tongue deviating paddle 32. Likewise, as seen in FIG. 3, a midline rod 30 may be provided sized and shaped complementary to through joint aperture slot or hole defined by sidewalls 28 in ball joint 27 of anterior strut 26, to connect, locate, and secure a tongue-depressing paddle 40.

In an embodiment, a tongue deviating paddle 32 may be provided in generally oval or tear-drop shaped configuration. However, any convenient figuration may be utilized, and the device shall in no way be considered to limited structures and uses to such shapes as may be suggested for an embodiment In an embodiment, a tongue-deviating paddle 32, or a tongue-depressing paddle 40, may be provided with a midline rod 30A that will fit through the anterior strut 26 and protrude outward from the front of the dental arch assembly 60 for control during the fitting and placement stage. As seen in FIG. 2, a tongue-deviating paddle 32 may have a working surface 41 that at least in part has a concave surface toward a patient's tongue T (see FIG. 1, not shown in FIG. 2.) The tongue-deviating paddle may also have a convex surface 43 on a non-working side, that is, a side away from a patient's tongue. Affixed to, or provided as a part of a tongue-deviating paddle 32, a mount 34 may be provided for securing thereto a posterior stabilizing rod 22. Such posterior stabilizing rod may, in an embodiment, be sized and shaped to fit through the appropriate guides in the form of through joint aperture slots or holes defined by sidewalls 18 (alternately, guides defined in the form of through joint aperture slots or holes defined by sidewalls 20) in one of one or more posterior struts, which are here shown as struts 14 and 16, in order to locate and secure tongue-deviating paddle 32, so as to hold the tongue toward the contra lateral (opposite) side. The tongue-deviating paddles 32 may take different forms and sizes (e.g., small, medium, or large) and be configured to deviate to the right or to deviate to the left of a patient, depending on the side of a patient's mouth where their cancer that requires treatment is located.

A tongue-deviating paddle 32 may be provided in a generally oval shaped or tear-drop-shaped tongue protection element PE having a mount 34 configured to receive at a first end $22_1$ or $24_1$ of one of the posterior stabilizing rods 22 or 24, respectively. In an embodiment, as may be appreciated by reference to FIG. 15A, mount 34 may be provided in the form of a seat formed in the protective element PE (e.g. tongue-deviating paddle 32) containing a spherical or ball type joint wherein ball 34B has a rod-receiving partial aperture defined by interior sidewalls wall $34_C$ and interior end wall $34_E$.

In an embodiment, a protective element PE such as a tongue-deviating paddle 32 may further include a housing 36 that is sized and shape to receive a midline rod $30_A$. In an embodiment, the housing 36 may be defined by interior sidewalls $36_C$ and by an endwall $36_E$, as noted in FIG. 14. In an embodiment, a housing 36 may be mounted at or near an anterior end $36_A$ of a tongue-deviating paddle 32, and configured to receive a first end $30_{A1}$ of midline rod $30_A$.

As seen in FIGS. 3 and 7, a tongue-depressing paddle 40 may be provided with a tongue protection element 41. Such tongue protection element 41 may be provided in a generally oval-shape, or with a rounded triangular shape, or with a trapezoidal-shape, as suitable in particular circumstances. In an embodiment, joints 42 and/or 44 may be provided, and mounted on a first side 43 of the paddle 40. The joints 42 and/or 44 may be provided as ball mount joints, in that balls $42_B$ and $44_B$, respectively, are provided with spherical freedom of movement in joints 42 and/or 44. In an embodiment, as noted in a cross-sectional view provided in FIGS. 15B and 15C, balls $42_B$ and $44_B$ may be provided with rod-receiving partial apertures defined by interior sidewalls walls $42_C$ and $44_C$, and interior end walls $42_E$ and $44_E$, respectively. The rod-receiving partial apertures defined by the just mentioned features are configured to receive and seat the posterior stabilizing rods 22 and 24, and more particularly a first end $22_1$ or $24_1$ of such rods, as noted in broken lines in FIGS. 15B and 15C. In an embodiment, the tongue-depressing paddle 40 may be provided with a housing 46 configured to receive the midline rod 30, which in an embodiment may be of the same configuration as described above as regards housing 36.

Embodiments of the intra-oral device 200 will now be further described with reference to FIGS. 2, 3 and 4. FIG. 2 illustrates an embodiment of an intra-oral device 200 configured with a tongue-deviating paddle 32. However, it must be understood that the tongue-deviating paddle 32 components and connecting parts as shown configured in FIG. 2 are interchangeable, and thus may be replaced by similar elements of different sizes, or of either right hand or of left hand configuration, and such alternate configuration will provide the tissue positioning functionality as described herein. As assembled, the intra-oral device 200 includes two elongate, essentially U-shaped members, namely an upper member 10 and a lower member 12. The upper member 10 and the lower member 12 are shown coupled together by struts 15 and 16.

Figure 12:
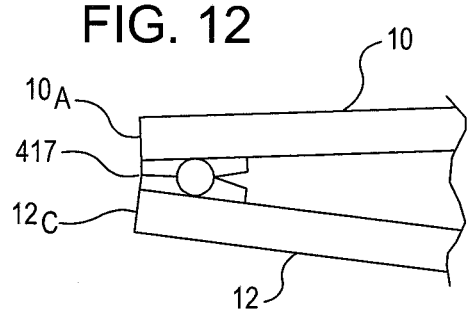

As seen in FIG. 12, in another embodiment, an upper member 10 may be coupled to a lower member 12 using a moveable joint 417. Alternatively, upper member 10 and lower member 12 may be directly and fixedly attached together, as generally shown in FIGS. 2, 3, 6 and 8, for example.

Figure 4:
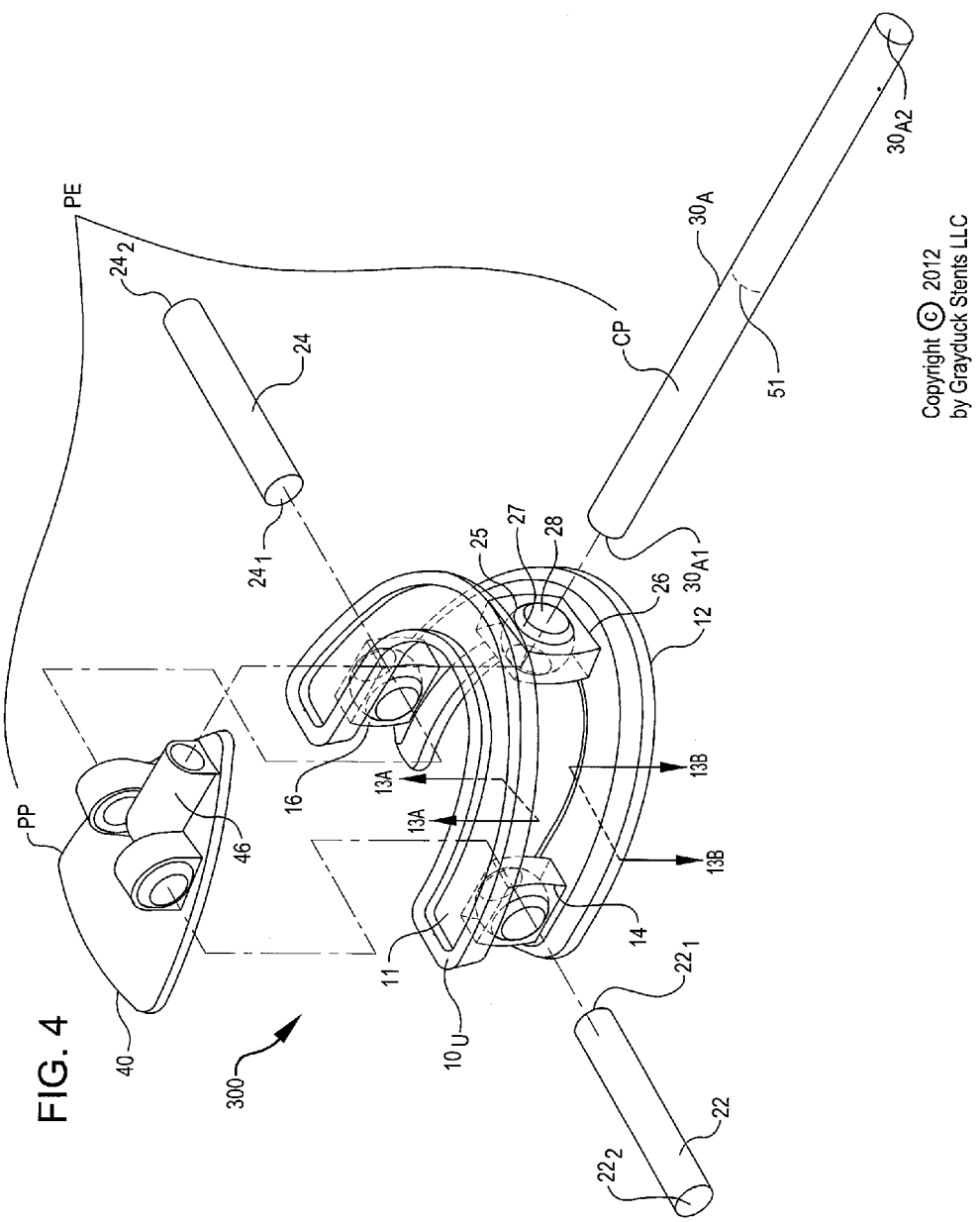
Figure 5:
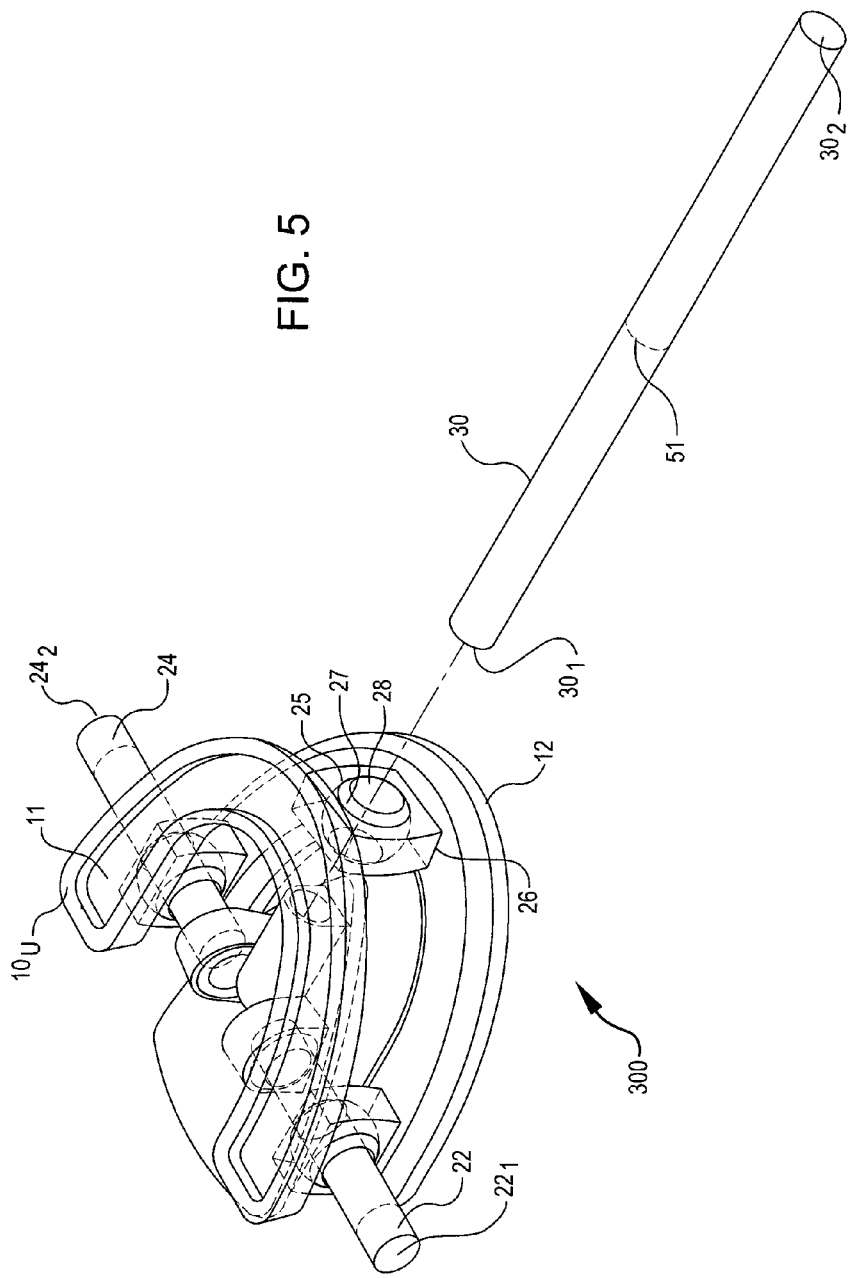
Figure 6:
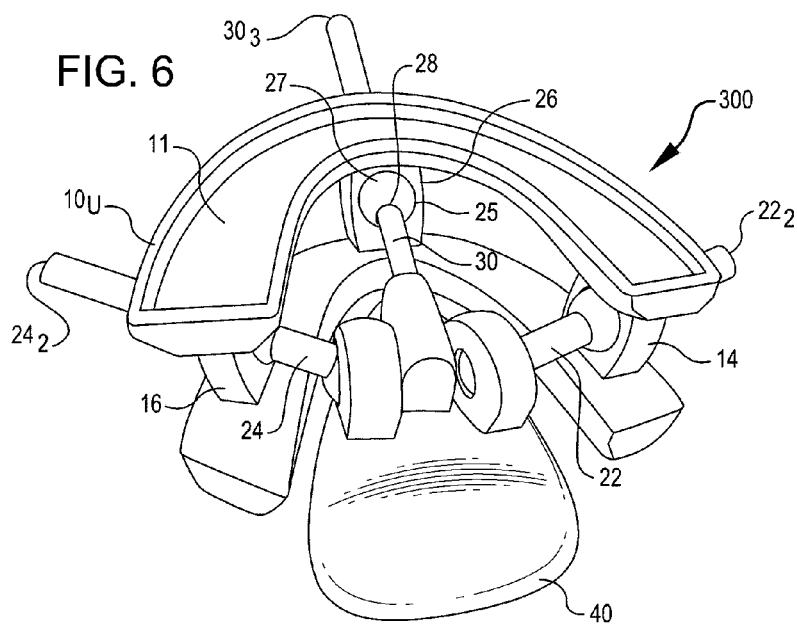

FIG. 13A illustrates a cross-section taken at line 13A-13A of FIG. 4 of an upper dental arch member 10. As shown in FIG. 13A, the upper dental arch member 10 may be provided with an upper receiving trough 11, which in an embodiment may generally be U-shaped. As noted above, the upper receiving trough 11 may be adapted to be filled with fill-in material $11_F$. The fill-in material $11_F$ may be provided in the form of a moldable plastic or similar moldable material that may be cured once molded. Molded material may be provided responsive to the size and shape $10_M$ of a patient's maxillary teeth 50, or edentulous arch, as suggested by illustrations provided in FIGS. 1, 4, and 13A.

FIG. 13B illustrates a cross-section taken at line 13B-13B of FIG. 4 of a lower dental arch member 12. As shown in FIG. 13B, the lower dental arch member 12 may be provided with a lower receiving trough 13, which in an embodiment may generally be U-shaped. As noted above, the lower receiving trough 13 may be adapted to be filled with fill-in material $12_F$. The fill-in material $12_F$ may be provided in the form of a moldable plastic or similar moldable material that may be cured once molded. A mold may be provided responsive to the size and shape of a patient's mandibular teeth 52, or edentulous arch, as suggested by illustrations provided in FIGS. 1, 4, and 13B.

When assembled an intra-oral device 200 may include an upper dental arch member 10 having upper molded surface $10_M$ and a lower dental arch member 12 with lower molded surface $12_M$ that as joined together, such as by struts 16 provide a dental arch assembly 60 which acts as an inter-maxillary scaffold. The dental arch assembly 60 thus holds a patient's maxillary teeth/arch 50 and mandibular teeth/arch 52 (see, for example, the position of patient's teeth 50 and 52 and angle alpha a in FIG. 1) apart in a repeatable position in three-dimensional space, at a selected angle alpha a of opening, and, as may be possible with suitable patient tolerance consistent with medical objectives, at suitable forward or rearward positioning of the mandibular teeth/arch 52 in relation to the position of the maxillary teeth/arch 50.

In an embodiment, a dental arch assembly 60 should be considered to be an intra-oral device, even without the use of a protective element such as tongue deviating paddles 32 or tongue-depressing paddles 40 or the like. In any event, when a desired or prescribed opening position of a patient's mouth is achieved with the intermaxillary dental arch assembly 60 portion of the intra-oral device, 200, the device then additionally is used to provide supports for a protective element such as a "tongue paddle"—that is a tongue-deviating paddle $32_R$, $32_L$, or tongue-depressing paddle 40—and thus a selected paddle then displaces a patient's tongue in a prescribed direction and position.

After a dental arch assembly 60 is constructed, a protective element PE including protective portions PP (see FIG. 8) such as tongue paddle $32_R$ or $32_L$ may be inserted into a patient's mouth and loosely attached by way of an adjustable guide to the dental arch assembly 60. Using a posterior stabilizing rod 22 as a stabilizing device, rotating the tongue-deviating paddle $32_L$ or $32_R$ using midline rod 30A and the adjustable guide 27 as a fulcrum point, a patient's tongue may be positioned to a desired location. In an embodiment, once the patient's tongue T is in a suitable location, the anterior strut 26 and posterior strut 14 (or 16, as applicable) may be fixed to midline rod 30A and posterior stabilizing rod 22. In an embodiment, a locking mechanism 70 (e.g., compression fitting) may be utilized to fix in place any one or more of posterior stabilizing rods 22 or 24, or midline rods 30, or $30_A$ (each of which is more fully described elsewhere herein). In an embodiment, fixation into a secure working position may be accomplished using a bonding agent, such as a curable bonding agent known in the field, such as light-cured acrylic, or by other methods such as by fusing the components with cyanoacrylate compositions or similar bonding agents. In any event, the objective is to assemble an intra-oral device, for example device 100, 200, or 300, into a secure configuration, and to lock the protective element such as a tongue-deviating paddle (e.g., $32_L$ or $32_R$) or a tongue-depressing paddle 40 into a final, secure position. In various embodiments, such locking mechanisms may be irreversible (e.g., cyanoacrylate fusion) or reversible (mechanical locking mechanism 70).

Referring back to FIG. 2, the intra-oral device 200 may include an oval-shaped or tear-drop shaped tongue protective element, e.g., tongue-deviating paddle 32. In an embodiment, a paddle (e.g. 32 or 40) may be positioned in the middle of the device 200. In an embodiment, a tongue deviating paddle 32 may be disposed within the device 200 such that certain freedom of movement (adjustment ability) of the tongue deviating paddle 32 within the device 200 is ensured. Ball joints 19 or 21 which are included in the struts 14 and 16, respectively, and similar structures 34 in tongue deviating paddle 32, or $42_B$ and $44_B$ in the tongue-depressing paddle 40, may be configured to allow a desired range of motion of a protective element (e.g. tongue paddles $32_R$, $32_L$, or 40) relative to the dental arch assembly 60. Such ball joints may be secured to their respective struts or paddles. In an embodiment, such assembly and fixation goal may be accomplished using a bonding agent, such as a curable bonding compound (e.g., a cyanoacrylate composition) once a tongue paddle (e.g., paddle $32_L$, $32_R$, or 40) is positioned in a desired location. For example, the tongue-deviating paddle 32 may be coupled through the mount 34 with the rod 22 disposed through the strut 14. The front end $32_A$ of the tongue-deviating paddle 32 may be connected with the midline rod $30_A$ disposed through the anterior strut 26. The described structure allows for movement at the front end $32_A$ of tongue-deviating paddle 32 when the midline rod $30_A$ is moved. The excess part of a midline rod $30_A$ may be removed (e.g., cut off or snapped off at broken line 51) once the tongue-deviating paddle (e.g. 32) is secured in a desired position, to provide a new second end $30_{A3}$ of midline rod $30_A$. Similarly, in an intra-oral device 300 using a tongue-depressing paddle 40, any excess part of a midline rod 30 may be removed (e.g., cut off or snapped off at broken line 51) once the tongue-depressing paddle (e.g. 40) is secured in a desired position, to provide a new second end 303 of midline rod 30.

As shown in FIG. 2, and further described below, the tongue-deviating paddle 32 may be disposed generally vertically relative to the intermaxillary supporting dental arch assembly 60. While in this FIG. 2 the tongue-deviating paddle 32 illustrated is configured to provide a tongue deviation to the left (relative to the patient), a "right hand" version of a tongue-deviating paddle $32_R$ may be configured and mounted similarly to that of the "left hand" version $32_L$. In an embodiment, the upper dental arch member 10 and/or lower dental arch member 12 may be configured to provide independent support for a protective element such as tongue-deviating paddle $32_R$ or $32_L$ or tongue-depressing paddle 40. For example, a tongue-deviating paddle 32 may be attached to a middle section (somewhere about the center of the U-shape) of the upper dental arch member 10 or to a middle section (somewhere about the center of the U-shape) of the lower dental arch member 12.

Turning again to FIG. 3, an embodiment of an intra-oral device 300 will now be further described. FIG. 3 illustrates an example assembly for an intra-oral device 300 that includes a tongue-depressing paddle 40. Similar to the tongue-deviating paddles 32, the tongue-depressing paddle 40 may utilize a midline rod 30 that fits through a ball joint 27 of an anterior strut 26. In an embodiment, a tongue-depressing paddle 40 may be generally a rounded triangular, trapezoidal or oval-shaped and may be positioned generally horizontally as shown in FIG. 3. Like the tongue-deviating paddles 32 described above, a tongue-depressing paddle 40 may be loosely fitted intra-orally into the dental arch assembly 60 (formed by the upper dental arch member 10 and lower dental arch member 12), and positioned using the midline rod 30. Once the tongue-depressing paddle 40 is in a selected position, the tongue-depressing paddle 40 may be immobilized and thus fixed in place via midline rod 30 and anterior strut 26. Then, the midline rod 30 may be shortened as desired. Also, posterior stabilizing rods 22 and 24 may be added for additional strength, and secured to the dental arch assembly 60 and to the tongue-depressing paddle 40. Suitable locking mechanisms or curable bonding agents or the like as mentioned elsewhere herein may be utilized as appropriate to secure and ensure the intended service of the intra-oral device.

Turning again to FIGS. 1 and 2, in an intra-oral device 100 or 200 as set out in such drawing figures, respectively, the upper dental arch member 10 defines an upper plane 90 approximating a plane along the occlusal surfaces 92 of a patent's maxillary teeth 50 or edentulous arch. In various embodiments, as may be understood by additional reference to FIG. 8, a protective element PE, including protective portion PP (e.g., tongue-deviating paddle $32_R$ or $32_L$) and connector portion CP (e.g., midline rod 30 or 30A) may be deployed in a configuration roughly perpendicular to the upper plane 90. In various embodiments, such roughly perpendicular configuration will vary, anywhere from a precisely perpendicular orientation at ninety (90) degrees to upper plane 90, up to as much of an offset as plus or minus forty five (45) degrees from a perpendicular orientation.

Turning to FIG. 1 for orientation with respect to dental arch member 60, and to FIGS. 3, 4, and 7 as regards an intra-oral device 300, the lower dental arch member 12 defines a lower plane 94 (see FIG. 1) approximating a plane along the occlusal surfaces 96 of a patent's mandibular teeth 50 or edentulous arch. In various embodiments, as may be understood by additional reference to FIG. 4, a protective element PE, including protective portion PP (e.g., tongue-depressing paddle 40) and connector portion CP (e.g., midline rod 30A) may be deployed in a configuration with protective portion PP oriented roughly parallel to the lower plane 90. In various embodiments, such roughly parallel configuration will vary, anywhere from a precisely parallel orientation to lower plane 94, in many embodiments, up to as much of a downward or upward angle (using connector portion CP such as midline rod $30_A$ for evaluation of the angle) of plus or minus forty five (45) degrees from a parallel orientation. In an embodiments for an intra-oral device 300 utilizing a tongue-depressing paddle 40, first posterior stabilizing rod 22 and second posterior stabilizing rod 24 may be structured in an anhedral configuration, where the rods 22 and 24 are extending upward from their respective guides G at struts 14 and 16 toward tongue-depressing paddle 40. In an embodiments for an intra-oral device 300 utilizing a tongue-depressing paddle 40, first posterior stabilizing rod 22 and second posterior stabilizing rod 24 may be structured in a dihedral configuration, where the rods 22 and 24 are extending downward from their respective guides G at struts 14 and 16 toward tongue-depressing paddle 40. In an embodiments for an intra-oral device 300 utilizing a tongue-depressing paddle 40, first posterior stabilizing rod 22 and second posterior stabilizing rod 24 may be structured in a neutral configuration, where the rods 22 and 24 extending substantially horizontally from their respective guides G at struts 14 and 16 toward tongue-depressing paddle 40.

Any of the dental arch assemblies 60, and other components used in intra-oral devices 100, 200 or 300 may be customized for a particular patient. Similarly, the shape of a tongue paddle (e.g. paddles $32_L$, $32_R$, or 40) may be adjusted (by material removal, or/and by material addition) to optimize the particular shape of the device to fit a patient's tongue or their other oral tissue limitations (surgical scars, for example) for comfort and/or ideal management. In operation, when the customized device is inserted into the patient's mouth, the tongue paddle (e.g. paddles 32 or 40) will shift the location of a patient's tongue so as to either avoid or reduce adverse effects of head and neck cancer radiation treatment, thus protecting or stabilizing the tongue tissues. The materials selected may optimally be capable of withstanding several weeks of daily high-dose radiation exposure. In an embodiment, an intra-oral device 100, 200 or 300 may be manufactured of a radiation resistant material (thus, in an embodiment, having low radiation absorption and scatter. Accordingly, an intra-oral device 100, 200 or 300 may be manufactured using any suitable material, for example plastics, acrylics, carbon fibers, or other materials having properties consistent with applicable requirements, including various governmental regulations for medical treatment devices used in oral service in humans.

The fill-in material $11_F$ and $13_F$ for the upper member 10 and lower member 12 as described above in reference to FIG. 13A, may include a suitable material having a moldable property. For example, the fill-in material may be made of a customizable material such as Triad® acrylic, a polyether, or polyvinylsiloxane, or other functionally similar materials. When the device 200 or 300 is inserted into the patient's mouth, the patient "molds" the surfaces $10_M$ on the upper member 10, and $12_M$ on the lower member 12, by biting into the fill-in material, which in an embodiment, may be subsequently hardened, for example either autocatalytically or via application of a bright photoactivating light. In this manner, the surfaces $10_M$ and $12_M$ replicate the occlusal surfaces of a particular patient's maxillary teeth 50 and mandibular teeth 52 or comparable edentulous arch forms. The devices 200 or 300 may also be customized, such as by addition of light-cured acrylic to add devices such as lead-lined lip bumpers, cheek bumpers near metallic crowns, and the like.

In the foregoing description, numerous details have been set forth in order to provide a thorough understanding of the disclosed exemplary embodiments for an intra-oral device for positioning certain oral tissue during radiation treatment. The purpose of the intra-oral devices described here is to provide a wide range of flexibility to give the end user of the device as much latitude to customize and idealize its application for the maximum benefit of the patient. However, certain of the described details may not be required in order to provide useful embodiments, or to practice selected or other disclosed embodiments. Further, the description may include, for descriptive purposes, various relative terms such as surface, at, adjacent, proximity, near, on, onto, and the like. Such usage should not be construed as limiting. Terms that are relative only to a point of reference are not meant to be interpreted as absolute limitations, but are instead included in the foregoing description to facilitate understanding of the various aspects of the disclosed embodiments. Various components are described which may be employed alternatively, yet be included in a kit or product package to enable an end user to select the optimal components for use in a particular situation. Accordingly, procedures utilizing the intra-oral device described herein, and the method(s) described herein may be utilized as multiple discrete operations, in a manner that is most helpful in a particular circumstance. However, the order of description should not be construed as to imply that such alternatives are necessarily order dependent, or that use of various components is necessarily in the alternative. Also, the reader will note that the phrase "in one embodiment" has been used repeatedly. This phrase generally does not refer to the same embodiment; however, it may. Finally, the terms "comprising", "having" and "including" should be considered synonymous, unless the context dictates otherwise.

Various aspects and embodiments described and claimed herein may be modified from those shown without materially departing from the novel teachings and advantages provided by this invention, and may be embodied in other specific forms without departing from the spirit or essential characteristics thereof. Embodiments presented herein are to be considered in all respects as illustrative and not restrictive or limiting. This disclosure is intended to cover methods and apparatus described herein, and not only structural equivalents thereof, but also equivalent structures. Modifications and variations are possible in light of the above teachings. Therefore, the protection afforded to this invention should be limited only by the claims set forth herein, and the legal equivalents thereof.

The invention claimed is:

1. An intra-oral device for use in anti-cancer radiation treatment of the head and/or neck of a patient with or without maxillary and/or mandibular teeth, for positioning oral tissues in said patient, said device comprising:
(a) a dental arch assembly, said dental arch assembly comprising
an upper dental arch member having a first end and a second end, said upper dental arch member configured for engagement with the maxillary teeth or maxillary edentulous arch of said patient;

a lower dental arch member having a third end and a fourth end, the lower dental arch member configured for engagement with the mandibular teeth or mandibular edentulous arch of the patient; and at least one strut including a first posterior strut and a second posterior strut that each couple the upper dental arch member to said lower dental arch member, said at least one strut comprising an anterior strut, said at least one strut fixedly attaching said upper dental arch member and said lower dental arch member together into a fixed, spaced-apart position, and wherein one or more of said at least one strut further comprises an adjustable guide portion; and (b) a protective element, said protective element comprising a protective portion and a connector portion, said protective element coupled to said dental arch assembly, said protective element fixedly attachable to said at least one strut, said protective element configured to engage oral tissues of said patient;

(c) whereby after said protective element is fixedly attached, said intra-oral device is adapted to position oral tissues of said patient so as to minimize exposure of said patient's oral tissues to radiation during said radiation treatment; and (d) a first posterior stabilizing rod connector, and wherein said adjustable guide portion is provided in at least one of the first posterior strut and the second posterior strut, and wherein said protective element further comprises a mount comprising a first ball joint configured to receive said first posterior stabilizing rod connector, and wherein said first posterior stabilizing rod connector provides a structural member between one of said adjustable guide portion and said first ball joint, so that at time of fabrication, said first stabilizing rod connector adjustably couples said protective element to said dental arch assembly.

2. An intra-oral device as set forth in claim 1, wherein said protective element, at time of fabrication, is adjustably positionable with respect to said dental arch assembly at one of said adjustable guide portions in one of said at least one struts, in two or more of (a) pitch axis, (b) roll axis, (c) yaw axis, and (d) linear axis.

3. An intra-oral device as set forth in claim 1, wherein said connector portion of said protective element, at time of fabrication, is adjustably positionable with respect to said dental arch assembly at one of said adjustable guide portions in one of said at least one struts, in two or more of (a) pitch axis, (b) roll axis, (c) yaw axis, and (d) linear axis.

4. An intra-oral device as set forth in claim 1, wherein the upper dental arch member defines an upper plane approximating a plane along occlusal surfaces of a patient's maxillary teeth or edentulous arch, and wherein said protective element is deployed in a configuration approximately perpendicular to said upper plane.

5. An intra-oral device as set forth in claim 1, wherein the lower dental arch member defines a lower plane approximating a plane along occlusal surfaces of a patient's mandibular teeth or edentulous arch, and wherein said protective element is deployed in a configuration approximately parallel to said lower plane.

6. An intra-oral device as set forth in claim 1, wherein said protective element comprises a working side including a concave surface.

7. An intra-oral device as set forth in claim 1, wherein said protective element comprises a tongue-deviating paddle.

8. An intra-oral device as set forth in claim 7, wherein said tongue-deviating paddle is sized, shaped, and configured to move said patient's tongue to the patient's left.

9. An intra-oral device as set forth in claim 7, wherein said tongue-deviating paddle is sized, shaped, and configured to move said patient's tongue to the patient's right.

10. An intra-oral device as set forth in claim 1, wherein said intra-oral device further comprises a second posterior stabilizing rod connector, and wherein one of said adjustable guide portions is provided (a) at a first posterior strut and (b) at a second posterior strut, and wherein said protective element further comprises a second ball joint configured to receive said second posterior stabilizing rod connector, and wherein said second posterior stabilizing rod connector provides a structural member between one of said adjustable guide portions and said second ball joint, so that at time of fabrication, said second posterior stabilizing rod connector adjustably couples said protective element to said dental arch assembly.

11. An intra-oral device as set forth in claim 10, wherein said protective element comprises a tongue-depressing paddle.

12. An intra-oral device as set forth in claim 10, wherein said connector portion comprises a first end and a second end, and wherein said protective element comprises a housing configured to receive said first end of said connector portion.

13. An intra-oral device as set forth in claim 12, wherein said connector portion comprises a midline rod.

14. An intra-oral device as set forth in claim 1, wherein said protective portion and said connector portion of said protective element are separable.

15. An intra-oral device as set forth in claim 1, wherein said upper dental arch member further comprises an upper receiving trough, said upper receiving trough adapted to receive a moldable compound for fabrication into a bite pad for secure receipt of the occlusal surface of said patient's maxillary teeth or edentulous arch.

16. An intra-oral device as set forth in claim 1, wherein said lower dental arch member further comprises a lower receiving trough, said lower receiving trough adapted to receive a moldable compound for fabrication into a bite pad for receipt of the occlusal surface of said patient's mandibular teeth or edentulous arch.

17. A kit for fabrication of an intra-oral device, said intra-oral device for positioning of oral tissues of a patient during anti-cancer radiation treatment of the head and/or neck of said patient, said kit comprising:

at least one upper dental arch member adapted to engage said patient's maxillary teeth or maxillary edentulous arch;

at least one lower dental arch member adapted to engage said patient's mandibular teeth or mandibular edentulous arch;

a plurality of struts, said plurality of struts each sized and shaped for interfitting engagement between an upper dental arch member and a lower dental arch member wherein said upper dental arch member and said lower dental arch member are joined together by said plurality of struts into a fixed, spaced-apart relationship, said plurality of struts comprising an anterior strut that fixedly attaches together said at least one upper dental arch member and said at least one lower dental arch member, and wherein at least one of said plurality of struts further comprise an adjustable guide portion, wherein said adjustable guide portion in said plurality of struts further comprises a ball joint, said ball joint adapted for motion in one or more of (a) pitch axis, (b) roll axis, and (c) yaw axis; and one or more protective elements fixedly attachable to at least one of said plurality of struts, said one or more protective elements adapted to engage oral tissues of said patient, said protective elements each comprising a protective portion and a connector portion, said connector portion sized and shaped for adjustable engagement with said adjustable guide portion before being affixed thereto, so that after being fixedly attached, the one or more protective elements are positioned so that said intra-oral device is adapted to minimize exposure of said oral tissues of said patient to radiation during said radiation treatment.

18. The kit as set forth in claim 17, wherein the connector portion and the protective portion of at least one of said one or more said protective elements are separable.

19. The kit as set forth in claim 17, wherein said connector portion and said protective portion of said one or more protective elements are provided unassembled each to the other.

20. The kit as set forth in claim 17, wherein said connector portion comprises a midline rod having a first end and a second end.

21. The kit as set forth in claim 17, wherein said ball joint comprises a through joint aperture defined by inner sidewalls, and wherein said connector portion has a linear axis, and wherein said connector portion is sized and shaped for sliding engagement therewith, along said linear axis.

22. The kit as set forth in claim 17, further comprising one or more posterior stabilizing rods, said posterior stabilizing rods each having a first end and a second end, and sized and shaped for sliding engagement with a through joint aperture in one or more of said ball joints.

23. The kit as set forth in claim 22, wherein said protective element further comprises at least one adjustable mount, said adjustable mount sized and shaped for seating a first end of a posterior stabilizing rod.

24. The kit as set forth in claim 17, wherein said upper dental arch member further comprises an upper receiving trough, said upper receiving trough adapted to receive a moldable compound for fabrication into a bite pad for receipt of occlusal surfaces of said patient's maxillary teeth or edentulous arch.

25. The kit as set forth in claim 17, wherein said lower dental arch member further comprises a lower receiving trough, said lower receiving trough adapted to receive a moldable compound for fabrication into a bite pad for receipt of occlusal surfaces of said patient's mandibular teeth or edentulous arch.

26. The kit as set forth in claim 17, wherein said protective element comprises a tongue-deviating paddle.

27. The kit as set forth in claim 26, wherein said tongue deviating paddle comprises a concave shape adapted to displace said patient's tongue to the left.

28. The kit as set forth in claim 26, wherein said tongue deviating paddle comprises a concave shape adapted to displace said patient's tongue to the right.

29. The kit as set forth in claim 17, wherein said protective element comprises a tongue-depressing paddle.

30. The kit as set forth in claim 17, wherein said plurality of struts comprises two or more posterior struts.

31. The kit as set forth in claim 17, further comprising a bonding compound, said bonding compound adapted for attachment of selected components of said kit, each to the other.

32. The kit as set forth in claim 17, further comprising a molding compound, said molding compound adapted for manufacture of bite pads corresponding to said patient's maxillary teeth and/or edentulous arch, and to said patient's mandibular teeth and/or edentulous arch.

33. A method for anti-cancer radiation treatment of the head and/or neck of a patient, comprising:

providing a kit for an intra-oral device as set forth in claim 17;

fabricating a dental arch assembly, said dental arch assembly including an upper dental arch member having a maxillary teeth and/or maxillary edentulous arch engaging surface, and a lower dental arch member having a mandibular teeth and/or mandibular edentulous arch engaging surface, wherein said maxillary teeth and/or maxillary edentulous arch engaging surface and the mandibular teeth and/or mandibular edentulous arch engaging surface are coupled by a plurality of struts to secure the maxillary teeth and/or maxillary edentulous arch and the mandibular teeth and/or mandibular edentulous arch into a fixed position relative each to the other with a defined gap therebetween, while preventing posterior or anterior movement of said patient's mandible;

wherein said plurality of struts comprises one or more posterior struts providing separation between said upper dental arch member and said lower dental arch member, and wherein said separation extends generally along a frontal portion of said dental arch assembly, whereat said dental arch assembly further comprises an anterior strut;

selecting a protective element for use, and adjustably coupling the protective element with said dental arch assembly via a ball joint adapted for motion in one or more of (a) pitch axis, (b) roll axis, and (c) yaw axis;

fixing said protective element at a selected position, so that said intra-oral device is adapted to secure said patient's tongue at a selected position with respect to said protective element, to secure the patient's tongue at a repeatable location while receiving radiation treatment.

34. The method as set forth in claim 33, wherein said spaced-apart relationship between the maxillary teeth and/or maxillary edentulous arch engaging surface and the mandibular teeth and/or mandibular edentulous arch engaging surface is determined at time of assembly, to accommodate different required treatment positions among a variety of patients.

35. The method as set forth in claim 33, wherein fixing said protective element at a selected position provides secure and repeatable positioning of said patient's tongue laterally or downward by said protective element.

36. An intra-oral device for use in radiation treatment of the head and/or neck of a patient with or without maxillary and/or mandibular teeth, for positioning oral tissues in said patient, said device comprising:

(a) a dental arch assembly, said dental arch assembly comprising an upper dental arch member having a first end and a second end, said upper dental arch member configured for engagement with the maxillary teeth or maxillary edentulous arch of said patient;

a lower dental arch member having a third end and a fourth end, the lower dental arch member configured for engagement with the mandibular teeth or mandibular edentulous arch of the patient; and a plurality of struts, said plurality of struts comprising an anterior strut, a first posterior strut, and a second posterior strut, said plurality of fixed struts fixedly attaching said upper dental arch member to said lower dental arch member in a fixed spaced apart working relationship, and wherein at least one of said plurality of struts further comprises an adjustable guide portion; and (b) a protective element, said protective element fixedly attachable to at least one of said plurality of struts, said protective element comprising a protective portion and a connector portion, said protective element coupled to said dental arch assembly at an adjustable guide portion, said protective element configured to engage oral tissues of said patient;

(c) whereby after said protective element is fixedly attached, said intra-oral device is adapted to position oral tissues of said patient so as to minimize exposure of said oral tissues to radiation during said radiation treatment; and (d) a first posterior stabilizing rod connector, and wherein said adjustable guide portion is provided in at least one of the first posterior strut and the second posterior strut, and wherein said protective element further comprises a mount comprising a first ball joint configured to receive said first posterior stabilizing rod connector, and wherein said first posterior stabilizing rod connector provides a structural member between one of said adjustable guide portion and said first ball joint, so that at time of fabrication, said first stabilizing rod connector adjustably couples said protective element to said dental arch assembly.

* * * * *